United States Patent
O'Regan

(10) Patent No.: US 9,175,314 B2
(45) Date of Patent: Nov. 3, 2015

(54) ANAEROBIC DIGESTION WITH SUPERCRITICAL WATER HYDROLYSIS AS PRETREATMENT

(75) Inventor: John O'Regan, Waterfall (IE)

(73) Assignee: Hollingford Limited, Cork (IE)

( * ) Notice: Subject to any disclaimer, the term of this patent is extended or adjusted under 35 U.S.C. 154(b) by 0 days.

(21) Appl. No.: 14/131,107

(22) PCT Filed: Jul. 2, 2012

(86) PCT No.: PCT/IE2012/000034
§ 371 (c)(1),
(2), (4) Date: Jan. 6, 2014

(87) PCT Pub. No.: WO2013/005202
PCT Pub. Date: Jan. 10, 2013

(65) Prior Publication Data
US 2014/0154767 A1    Jun. 5, 2014

(30) Foreign Application Priority Data

Jul. 6, 2011   (IE) .................................. 2011/0308

(51) Int. Cl.
*C12P 5/02*    (2006.01)
*C02F 11/04*   (2006.01)
*C02F 11/08*   (2006.01)

(52) U.S. Cl.
CPC .............. *C12P 5/023* (2013.01); *C02F 11/04* (2013.01); *C02F 11/086* (2013.01); *C02F 2209/02* (2013.01); *C02F 2209/03* (2013.01); *C02F 2209/06* (2013.01); *C02F 2209/44* (2013.01); *C02F 2301/08* (2013.01); *C02F 2301/10* (2013.01); *C02F 2303/06* (2013.01); *C02F 2303/10* (2013.01); *Y02E 50/343* (2013.01); *Y02W 10/30* (2015.05)

(58) Field of Classification Search
None
See application file for complete search history.

(56) References Cited

U.S. PATENT DOCUMENTS

| 4,594,164 A | 6/1986 | Titmas |
| 7,431,850 B2 | 10/2008 | Imai et al. |
| 2002/0070179 A1 | 6/2002 | Pilz et al. |

FOREIGN PATENT DOCUMENTS

WO   WO/2006/052206   *  5/2006

OTHER PUBLICATIONS

Rulkens, W., Energy & Fuels, 2008, vol. 22, p. 9-15.*
Goto et al., Journal of Supercritical Fluids, 1998, vol. 13, p. 277-282.*
IWA Publishing—"AquaCritox sewage and sludge treatment receives first commercial order", Mar. 2011, Water 21, 2 pages.*
International Search Report; PCT/IE2012/000034; Sep. 27, 2012.
H.Yoshida et al., "Efficient, high-speed methane fermentation for sewage sludge using subcritical water hydrolysis as pretreatment", Bioresouce Technology, Elsevier BV, GB, vol. 100, No. 12, Jun. 1, 2009, pp. 2933-2939, XP026027142, ISSN: 0960-8524, DOI: 10.1016/J.Biortech.2009.01.047.
International Preliminary Report on Patentability; PCT/IE2012/000034; Jan. 7, 2014.

* cited by examiner

*Primary Examiner* — Kade Ariani
(74) *Attorney, Agent, or Firm* — Studebaker & Brackett PC

(57) ABSTRACT

An hydrolysis stage of an anaerobic digestion (AD) process includes supercritical treatment in a reactor (R1). The treatment may use sub-stoichiometric oxygen so that there is not full oxidation. Effluent from the supercritical treatment may be used to pre-heat the organic matter in-feed to the supercritical treatment. There may be a second supercritical treatment in a second reactor (R2). This may have full stoichiometric oxygen, to oxidize the solids from the first reactor (R1) effluent. Furthermore, it provides heat for pre-heating its own in-feed and also that for the first reactor (R1). The output from the hydrolysis may be only clarified liquid, leading to particularly efficient downstream AD processes. The second supercritical treatment rector may oxidize also fed-back solids from the final stage of the AD.

15 Claims, 3 Drawing Sheets

ANAEROBIC DIGESTION WITH SUPERCRITICAL WATER HYDROLYSIS AS PRETREATMENT

INTRODUCTION

1. Field of the Invention

Figure 1:
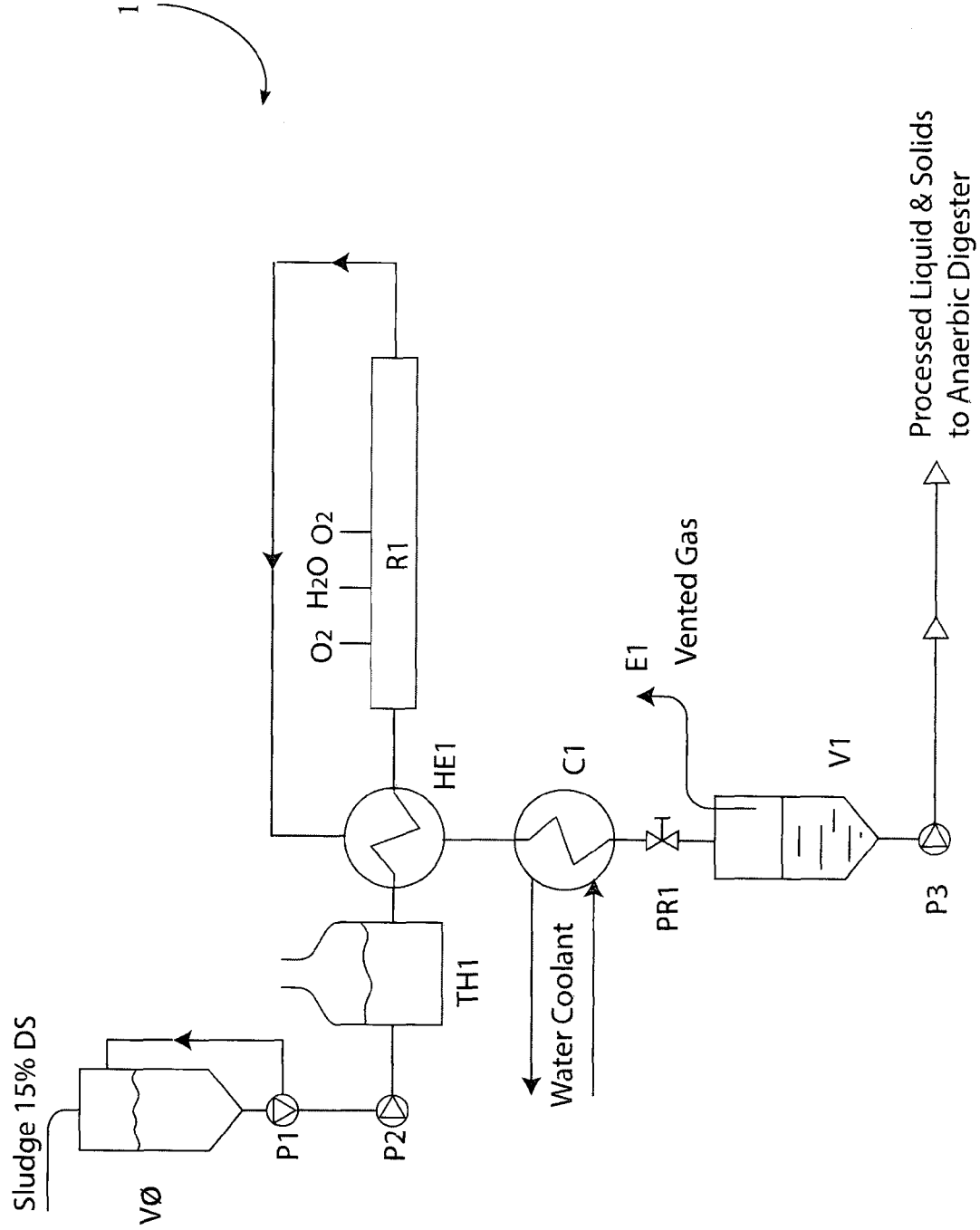

The invention relates to anaerobic digestion of organic waste.

2. Prior Art Discussion

Sludge or bio-solids are a by-product of the processing of sewage. Sewage sludge or bio-solids contain chemical energy in the form of cellulose, lignin, carbohydrate, proteins and lipids. A significant amount of this energy is in the form of bacteria cell mass. Sewage sludge also contains inorganic material such a silica, iron oxide and iron phosphate.

The water industry has sought to improve its efficiency by extracting as much energy as possible from the sewage sludge by subjecting it to anaerobic digestion.

Anaerobic digestion is a biological process whereby in the absence of oxygen, anaerobic bacteria reduce organic compounds to carbon dioxide ($CO_2$) and methane ($CH_4$). This practice reduces the sludge quantity and improves de-waterability, thus reducing the volume of sludge cake to be disposed of. The process may be regarded as having three stages, hydrolysis, acidogenesis, and methanogenesis.

Hydrolysis

The conversion of complex organic matter into lower molecular weight soluble compounds is called hydrolysis. Proteins are converted into amino acids, carbohydrates are transformed into soluble sugars, and lipids are converted into long-chain fatty acids and glycerol.

Thermal hydrolysis involves heating by steam of the substrate to a temperature in the region of 170° C. for a period of about 60 minutes and at pressures up to about 2 MPa, and rapid depressurisation. This causes bacteria cell walls to fracture and improves the amount of material available for digestion. The impact of this is reduced downstream anaerobic digester residence time and improved gas yield with corresponding sludge volume reduction.

While thermal hydrolysis accelerates the hydrolysis step, it does little to break down the hemicelluloses, cellulose and lignins found in vegetable matter and commonly present in significant quantity in sewage sludge and waste derived for food and other plant sources. Also, unfortunately the increased gas production is matched by an increased steam demand to drive the thermal hydrolysis unit, thus resulting in only marginal net gas yield available for export. Further, current thermal hydrolysis processes still leave a significant quantity of sludge. This is dewatered and disposed of to agriculture, landfill or incineration.

Acidogenesis

A diverse group of fermentative bacteria further break down the products of hydrolysis through acidogenesis into simple organic compounds. These compounds include volatile fatty acids, alcohols, and lactic acid, carbon dioxide, hydrogen, ammonia, and hydrogen sulphide gas.

Methanogenesis

The final step, methanogenesis, is the conversion of organic acids to methane gas. One pathway is the use of the carbon dioxide and hydrogen that was formed in the acidogenesis step. Another pathway is the conversion of acetate that was also formed in acidogenesis. Both these pathways are used by micro-organisms in the conversion of substrates to methane gas in anaerobic digestion of sludge or high strength waste.

In general, in the digestion of sludge derived from sewage treatment and food waste the anaerobic breakdown is slow and will typically be afforded a twenty to thirty day retention time with in the anaerobic digester. A typical conversion rate of organic content to biogas is approximately 30-50%.

The invention is directed towards achieving improved anaerobic digestion, with a shorter time and/or cleaner products. Further objectives include reduction in size of digester, elimination of organic solids and recovery of phosphate rich inert residue that has intrinsic value.

SUMMARY OF THE INVENTION

According to the invention, there is provided a process for anaerobic digestion of organic matter such as waste, the process comprising hydrolysis, acidogenesis, and methanogenesis, wherein the hydrolysis step includes supercritical treatment of the organic matter in a reactor by elevation of the organic matter to a temperature of at least 374° C. and a pressure of at least 221 bar for a supercritical residence time.

In one embodiment, the residence time is in the range of 30 s to 10 mins, preferably 60 s to 180 s.

In one embodiment, the supercritical treatment is performed in a reactor system comprising a bulk reactor followed by a plug flow reactor.

In one embodiment, the organic matter is of the type having a moisture content greater than 70%. Preferably, the organic matter comprises cellulose and lignins and other complex carbohydrates. In one embodiment, the organic matter has a pH value in the range of 3.5 to 8.0, preferably 4.5 to 7.5.

In one embodiment, oxidant is introduced for the supercritical treatment at a sub-stoichiometric level. In one embodiment, said sub-stoichiometric level is below 40%. In one embodiment, the treatment pressure is in the range of 221 bar to 300 bar. Preferably, the supercritical reactor temperature is in the rage of 374° C. to 400° C.

In one embodiment, the organic matter is pre-heated before the supercritical treatment. Preferably, the pre-heating raises the temperature to above 200° C. In one embodiment, said pre-treatment uses heat from effluent of the supercritical reactor.

In one embodiment, the effluent is directed through an annulus of a heat exchanger, and the inlet organic matter is fed through tubes of said heat exchanger. In one embodiment, the organic matter is re-circulated in a vessel before being pumped to the supercritical reactor.

In one embodiment, effluent from the supercritical treatment is delivered to a venting vessel from which gases are vented.

In one embodiment, effluent of the supercritical treatment is treated in a second supercritical reactor. In one embodiment, the effluent is processed by a gas-venting vessel and a cyclone separator before the second supercritical treatment.

In one embodiment, the effluent is further processed by addition of process water to provide a solids proportion in the range of about 10% to 14%, preferably about 12%.

In one embodiment, the second supercritical treatment is performed in a reactor with full stoichiometric oxygen, so that the second supercritical treatment effluent comprises substantially water and inert solids. Preferably, the effluent from the second supercritical treatment is used to pre-heat the in-feed to said second supercritical treatment. In one embodiment, the effluent from the second supercritical treatment is used to pre-heat the in-feed to the first supercritical treatment reactor, and the effluent from the first supercritical treatment reactor is used to pre-heat the in-feed to the second supercritical treatment reactor.

In one embodiment, the hydrolysis provides only clarified liquid to the acidogenesis stage.

In one embodiment, solids from the acidogenesis or methanogenesis stages are fed back to said hydrolysis stage. Preferably, said solids are fed back to the second supercritical reactor.

In another aspect, the invention provides an anaerobic digester hydrolysis apparatus comprising a supercritical treatment reactor arranged for supercritical treatment of organic matter by elevation of the organic matter to a temperature of at least 374° C. and a pressure of at least 221 bar for a supercritical residence time.

In one embodiment, the supercritical treatment reactor comprises a bulk reactor section followed by a plug flow reactor section. In one embodiment, the apparatus further comprises a heater arranged to pre-heat organic matter before entry to the supercritical treatment reactor.

In another embodiment, said heater is a heat exchanger arranged to use heat from effluent of the supercritical treatment reactor.

In one embodiment, the apparatus further comprises a pump and a vessel for re-circulating organic matter in a vessel before being pumped to the supercritical treatment reactor.

In one embodiment, the apparatus further comprises a venting vessel arranged to receive effluent from the supercritical treatment reactor and to vent gases from said effluent.

In one embodiment, the apparatus further comprises a second supercritical treatment reactor arranged to apply supercritical treatment to effluent of the first supercritical reactor.

In one embodiment, the apparatus further comprises a gas-venting vessel and a cyclone separator arranged to process said effluent before the second supercritical treatment reactor.

In one embodiment, the second supercritical treatment reactor is adapted to apply full stoichiometric oxygen, so that the second supercritical treatment effluent comprises substantially water and inert solids.

In one embodiment, the apparatus further comprises a heat exchanger arranged to pre-heat in-feed to said second supercritical treatment reactor using effluent from the second supercritical treatment reactor.

In one embodiment, the heat exchanger is arranged to pre-heat in-feed to the first supercritical treatment reactor.

In one embodiment, the apparatus comprises a separator arranged to supply only clarified liquid to an acidogenesis apparatus.

In one embodiment, the apparatus further comprises an inlet to receive solids from a downstream anaerobic digestion process and a conduit to deliver them to said second supercritical treatment reactor.

DETAILED DESCRIPTION OF THE INVENTION

Figure 2:
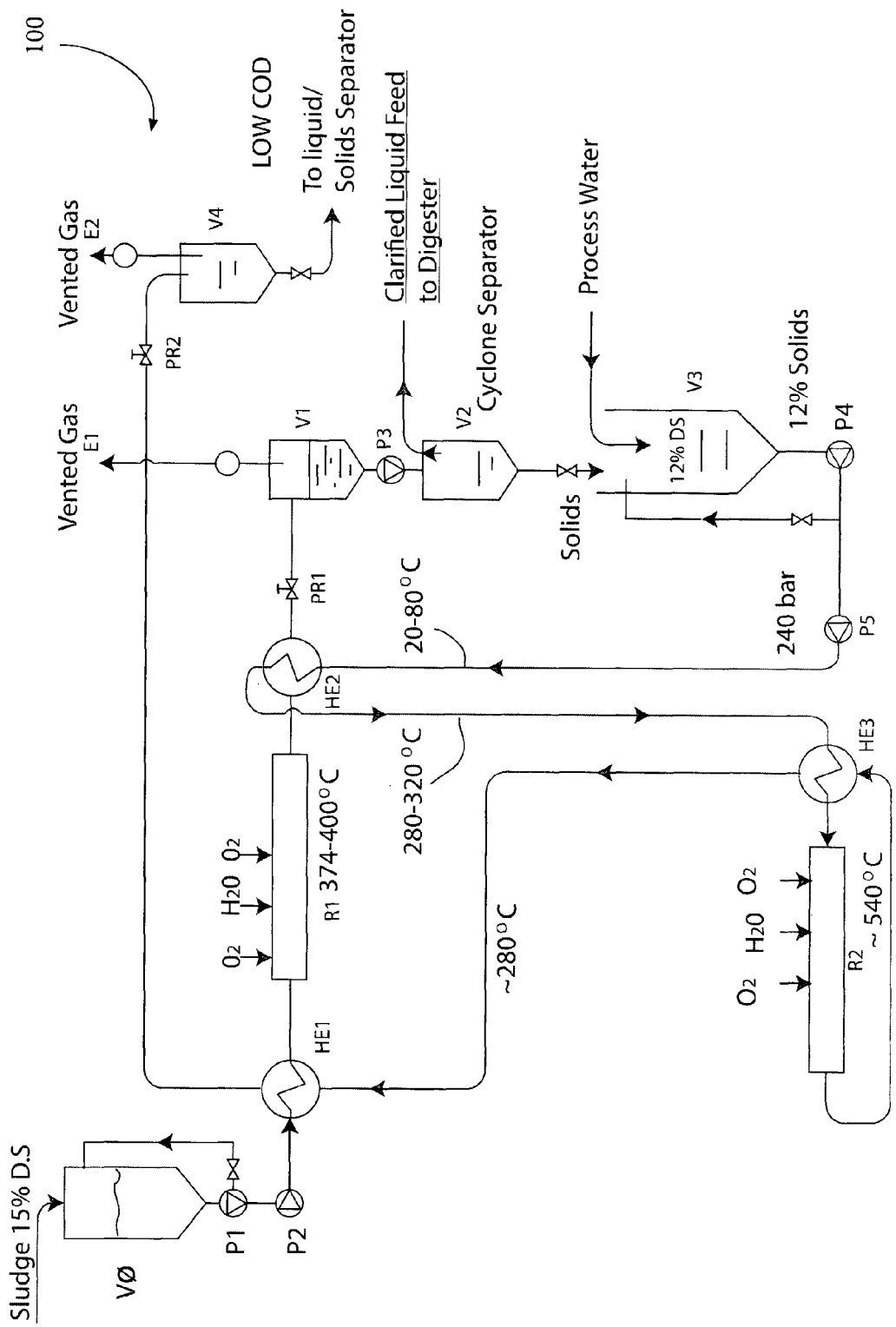
Figure 3:
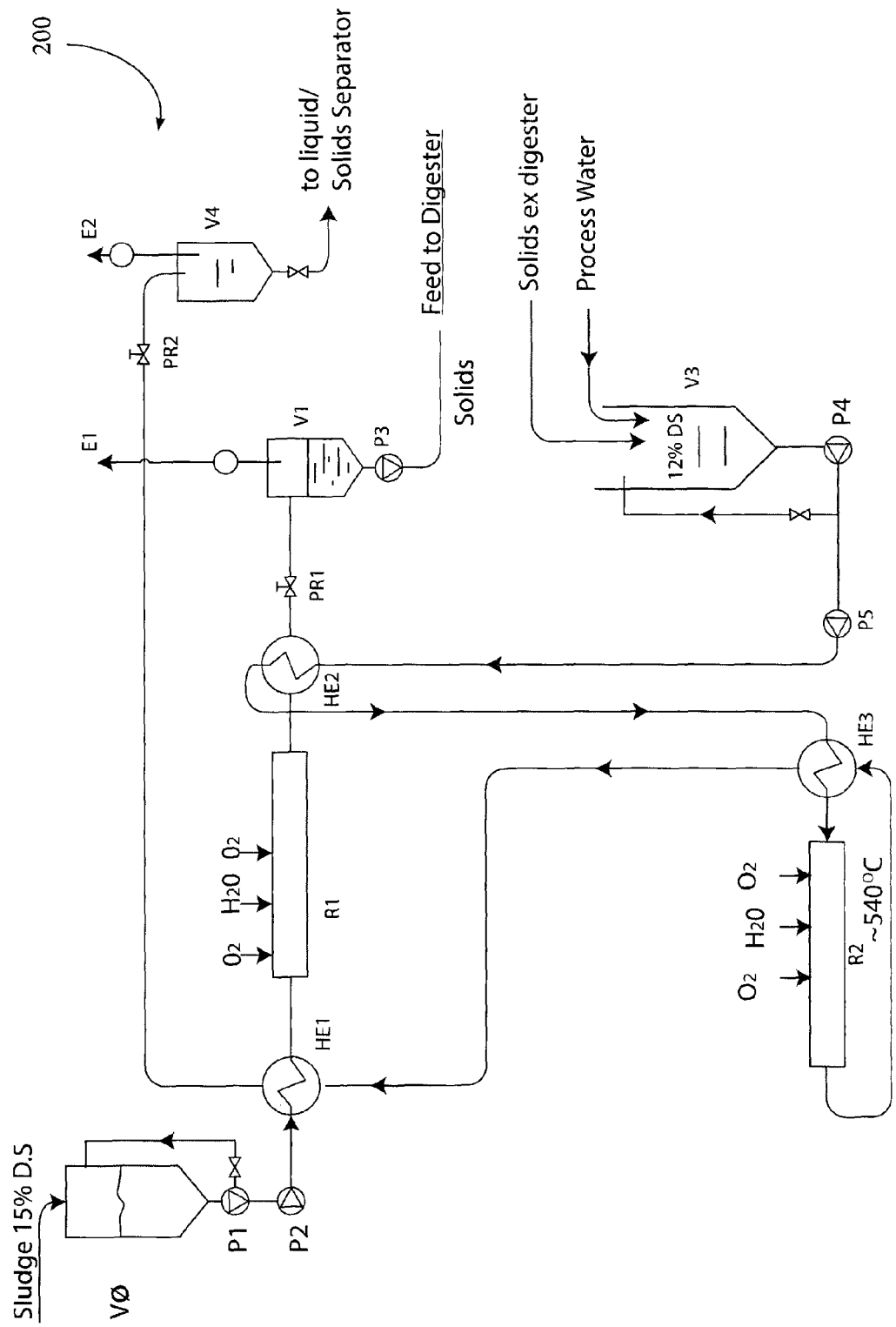

The invention will be more clearly understood from the following description of some embodiments thereof, given by way of example only with reference to the accompanying drawings in which:

FIG. 1 is a diagram illustrating an hydrolysis plant of the invention for an anaerobic digester; and FIGS. 2 and 3 are diagrams illustrating alternative hydrolysis plants of the invention.

In the invention, there is hydrolysis including supercritical treatment of sludge as part of an anaerobic digestion process. In one embodiment, the invention involves elevation of wet organic waste to at least the supercritical temperature and pressure of 374° C. and 221 bar in the absence of oxygen or with oxygen in sub stoiciometric quantity. In one embodiment, the organic matter is of the type having a moisture content greater than 70%. Preferably, the organic matter comprises cellulose and lignins and other complex carbohydrates. The organic matter may have a pH value in the range of 3.5 to 8.0, preferably 4.5 to 7.5. The waste stream is maintained under supercritical conditions for at least 30 seconds to cause rapid depolymerisation of polysaccharides such as lignin and cellulose. However, because the oxygen is sub-stoichiometric for the supercritical treatment there is not full oxidation. Therefore, there is an outlet hydrolysed waste stream for the downstream anaerobic digestion ("AD") steps. Also, there is much less steam generated and so there is no need to provide components for dumping of excess steam.

Under subcritical water conditions fats and greases will be subject to hydrolysis in the temperature region of 270° C. to 320° C. to form glycerol and fatty acids. Condensation reactions are not considered to take place due to the presence of water in single phase. As water becomes superheated it begins to act as a non-polar solvent. Thus the materials considered to be insoluble in water at 20° C. become increasingly soluble as the temperature increases beyond 300° C. due to the reduction in hydrogen bonding. Complex carbohydrates will initially undergo thermal depolymerisation. This is considered to begin at 220° C. and will proceed rapidly once temperatures of 300° C. are achieved.

The depolymerisation of cellulose and lignin results in the formation of a starch intermediate.

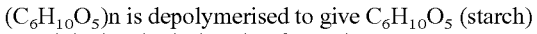
$(C_6H_{10}O_5)n$ is depolymerised to give $C_6H_{10}O_5$ (starch)
Starch is then hydrolysed to form glucose.
$C_6H_{10}O_5 + H_2O \rightarrow C_6H_{12}O_6$ (glucose).

This hydrolysis reaction is both time and temperature dependent.

As noted above, oxygen may be introduced in sub-stociometric quantity to cause partial oxidation. This partial oxidation reaction will cause the generation of heat to drive the above reactions. The sub-stoichiometric oxygen level is preferably below 40%

Hydrolysis with Delivery of Processed Liquids and Solids to Downstream AD Stages Referring to FIG. 1, sludge is fed to a vessel V0 with recirculation. The sludge dry solids ("DS") concentration is adjusted to 5%-20% and is re-circulated in the feed tank V0 using the pump P1. The pump P1 provides positive feed pressure to the suction side of a high pressure pump P2, which raises the pressure of the liquid to a minimum of 221 bar gauge pressure but this pressure can be as high as about 300 bar. The pump P2 also feeds the sludge from V0 through a heater TH1 and into a heat exchanger HE1 for pre-heating the sludge for a supercritical reactor R1. The reactor R1 may for example be of the type described in EP1812353

The pressurised feed is directed to the heater TH 1 so that the liquid's temperature is raised to a level that is sufficient to ensure that the exit temperature from the heat exchanger HE 1 is in the range of 200° C. to 400° C. but preferably 240° C. to 280° C.

The heated feed continues to the supercritical reactor R1 where oxygen in gaseous form is added under pressure in sub-stoichiometric amounts. The addition of oxygen causes some material to be oxidised, releasing thermal energy into the body of the pressurised fluid. This combination of temperature, pressure and short-lived free hydroxy radicals formed by the addition of sub-stoichiometric quantities of oxygen promotes hydrolysis and de-polymerisation leading to a significant quantity of the organic material present in the original sludge to be solubilised and converted to biodegradable materials such as organic acids. The effluent fluid is directed back to the annulus of HE1 where it gives up thermal energy to the incoming feed. The fluid is further cooled in a cooler C1. The cooled liquid is depressurised in a pressure-reducing system PR1 and directed to a gas liquid separator V1 where any gas such as carbon dioxide formed in the reactor is released from the liquid. The gas is emitted from the vessel V1 at emission point E1.

The treated sludge liquor is directed to the anaerobic digester by a pump P3 where the organic acids and other solubilised compounds present in the treated liquidate are readily converted to methane in the biological anaerobic digester acidogenesis and methanogenesis stages.

As water becomes superheated it begins to act as a non-polar solvent. Thus the materials considered to be insoluble in water at 20° C. become increasingly soluble as the temperature increases beyond 300° C. due to the reduction in hydrogen bonding.

Complex carbohydrates initially undergo thermal de-polymerisation. This is considered to begin at 220° C. and will proceed rapidly once temperatures of 300° C. are achieved. The depolymerisation of cellulose and lignin results in the formation of a starch intermediate. $(C_6H_{10}O_5)n$ is depolymerised to give $C_6H_{10}O_5$ (starch)

Starch is then hydrolysed to form glucose. $C_6H_{10}O_5 + H_2O \rightarrow C_6H_{12}O_6$ (glucose).

The thermally-induced reactions provide fatty acids, glycerol and glucose together some organic solids of undefined nature with inorganic solids including but not limited to silica, iron oxide and iron phosphate.

Hydrolysis with Delivery of Only Clarified Liquid to Downstream AD Stages

In this embodiment the feed to the downstream AD stages is a clarified liquid only, and so there are no solids to consider in the downstream digester plant and it will require only a few days of retention time, thus reducing the volume of the digester significantly. No sludge is therefore generated from the digester, all organic material present in the feed being converted to carbon dioxide and gas.

Referring to FIG. 2 an hydrolysis plant 100 is shown, and like parts are given the same reference numerals. As for the plant 1, the solids from the separation stage are prepared into slurry in the mixing tank V0 and pressurised by the high pressure pump P2 to greater than 20 MPa. The feed is then directed via a heat exchanger HE1 where it is heated to a minimum temperature of 240° C. The feed then enters the supercritical water reactor (hydrothermal reactor) R1 where oxygen is introduced in sufficient quantity to initiate an oxidation reaction. Further oxygen addition may be necessary to complete the oxidation reaction.

Like in the plant 1 the oxygen is added in R1 at a sub-stoichiometric level, and hence there is incomplete oxidation and therefore remaining effluent. This effluent gives off heat in a heat exchanger HE 2, and pressure is dropped in the pressure reducer PR1, and the effluent is delivered to a gas separation vessel V1, from which gas is vented at E1. A pump P3 pumps the solids into a cyclone V2, which provides the clarified liquid for the downstream AD processes. This is the final output of this hydrolysis plant 100.

The solids from the cyclone V2 are delivered to a vessel V3 to which process water is added to provide a 12% solids feed which is pumped by a pump P5 to about 240 bar. This feed is heated by HE2 from a temperature in the range of just above ambient (20° C. to 80° C.) to a temperature in the range of 280° C. to 320° C. It is further heated by a heat exchanger HE3 to a temperature greater than 374° C. and supercritical oxidation occurs to the full extent in a reactor R2, to which full stoichiometric oxygen is delivered. Steam with inert solids are delivered from the reactor R2 to the annulus of the heat exchanger HE3 to give up some heat for the R2 supply and further heat is given up in HE1 for the R1 supply. It finally is delivered to a vessel V4 where the gas is vented. The outlet from the vessel V4 is treated for recovery of the inert solids from clean water in a conventional manner.

As noted above, in R2 oxygen is introduced at stoichiometric rates to effect full oxidation of the residual organics. This is an exothermic reaction and is permitted to run to completion. The cooled liquid which is passed through the pressure reducer PR2 has its pressure reduced to approximately atmospheric. The gas-free liquid from V4 is sterile water with a typical Chemical Oxygen Demand of less than 20 mg/ltr.

It will be appreciated therefore, that the plant 100 provides only clarified liquid to the downstream AD processes, making them much simpler and more efficient. The solids are oxidised fully in the second supercritical reactor R2, and this also provides heat for its own feed and that to the first supercritical rector R1. Any residual solids are inert as is known n the field of supercritical treatment.

Hydrolysis with Treatment of Solids from the Downstream AD Processes

FIG. 3 shows a plant 200 which is variation on the plant 100. Heat from R1 effluent is recovered in HE 2 by directing the feed to the second reactor R2 from to the tube side of HE2 where it cools the effluent of R1. The feed is the directed to HE3 where it passes again through the tube side of HE3 and is heated to 280-400° C. but preferably 374-400° C. In R2 oxygen is introduced at stoichiometric rates to effect full oxidation of the residual organics. This is an exothermic reaction and is permitted to run to completion.

The hot effluent from R2 is directed to the annulus of HE3 where it gives up some of its thermal energy. The flow is then directed to HE1 where it passes through the annulus of HE1 to provide heating to the incoming feed. The cooled liquid is passed through pressure reduction PR1 where pressure is reduced to approximately atmospheric pressure. It then flows to V4 where any gas present is removed. The resultant gas-free liquid is directed to a solids/liquid separator where the inert solids are removed from the liquid. The liquid is sterile water with a typical Chemical oxygen demand of less than 20 mg/ltr.

In this embodiment, there is feedback of sludge exiting the downstream AD processes, into the vessel V3. It adds to the solids present in the feed to the second reactor R2. Thus the overall AD process does not have any final solids output, even though the hydrolysis does provide solids to the downstream processes.

It will be appreciated that the invention greatly improves the gas yield from an anaerobic digester without the need to consume a significant quantity of the $CH_4$ on site. Thus, up to 100% more gas is available for export or other use. It uses the properties of supercritical water to effect very rapid chemical change to the solubility and biodegradability of sludge (biosolids) so that a greater gas yield can be achieved from the anaerobic digester than would otherwise be achieved. The process utilises the embedded chemical energy that would normally remain undigested to drive the process, thus significantly improving the gas yield for export from the anaerobic digester process. Also, in some embodiments the process is a zero sludge process that produces an inert phosphorous rich by-product suitable for use in the phosphorous industry or elsewhere.

The invention is not limited to the embodiments described but may be varied in construction and detail. For example, the heat energy to drive the process can be supplied partially or fully by an external source such as a gas, oil, or an electric heating system.

The invention claimed is:

1. A process for anaerobic digestion of moisture containing organic matter, the process comprising the steps of hydrolysis, acidogenesis, and methanogenesis, wherein the hydrolysis step comprises supercritical treatment of the organic matter having a moisture content of greater than 70%, in a first supercritical reactor by elevation of the organic matter to a temperature of at least 374° C. and a pressure of at least 221 bar for a supercritical residence time in the range of 60 s to 180 s, wherein an oxidant is introduced at a sub-stoichiometric level for the supercritical treatment, and wherein the supercritical treatment provides an effluent and said effluent is delivered to a venting vessel from which gases are recovered, and at least some of said effluent is delivered to said acidogenesis step.

2. The process as claimed in claim 1, wherein the supercritical treatment is performed in said first supercritical reactor in a bulk reactor section followed by a plug flow reactor section.

3. The process as claimed in claim 1, wherein the organic matter comprises cellulose and lignins; and the organic matter has a pH value in the range of 3.5 to 8.0.

4. The process as claimed in claim 1, wherein said sub-stoichiometric level is below 40%.

5. The process as claimed in claim 1, wherein the supercritical treatment pressure is in the range of 221 bar to 300 bar; and wherein the organic matter comprises cellulose and lignins; and wherein the supercritical treatment temperature is in the range of 374° C. to 400° C.

6. The process as claimed in claim 1, wherein the organic matter is pre-heated before the supercritical treatment.

7. The process as claimed in claim 1, wherein the organic matter is pre-heated to above 200° C. before the supercritical treatment.

8. The process as claimed in claim 1, wherein the organic matter is pre-heated before the supercritical treatment using heat from said effluent, and said effluent is directed through an annulus of a heat exchanger, and the organic matter is fed through tubes of said heat exchanger.

9. The process as claimed in claim 1, wherein the organic matter is re-circulated in a vessel before being pumped to said first supercritical reactor.

10. The process as claimed in claim 1, wherein some of said effluent is treated in a second supercritical reactor; and wherein said effluent is processed by a gas-venting vessel and a cyclone separator before a second supercritical treatment in said second supercritical reactor.

11. The process as claimed in claim 1, wherein some of said effluent is treated in a second supercritical reactor; and wherein said effluent is processed by a gas-venting vessel and a cyclone separator before a second supercritical treatment in said second supercritical reactor; and wherein said effluent is further processed by addition of process water to provide a solid content in the range of about 10% to 14%.

12. The process as claimed in claim 1, wherein some of said effluent is treated in a second supercritical treatment in a second supercritical reactor; and wherein said second supercritical treatment is performed with full stoichiometric oxygen, so that the second supercritical treatment effluent comprises substantially water and inert solids.

13. The process as claimed in claim 1, wherein some of said effluent is treated in a second supercritical reactor, wherein there is effluent from said second supercritical reactor, and wherein said effluent from the second supercritical reactor is used to pre-heat said effluent fed to said second supercritical reactor.

14. The process as claimed in claim 1, wherein some of said effluent is used to pre-heat the organic matter fed to the reactor, and said effluent is used to pre-heat an in-feed to a second supercritical treatment reactor; wherein the hydrolysis provides only clarified liquid to the acidogenesis step; wherein solids from the acidogenesis or methanogenesis steps are fed back to said hydrolysis step; and wherein said solids are fed back to the second supercritical reactor.

15. The process as claimed in claim 1, wherein the organic matter has a pH value in the range of 4.5 to 7.5.

* * * * *